United States Patent [19]

Konishi et al.

[11] Patent Number: 5,508,759
[45] Date of Patent: Apr. 16, 1996

[54] VISUAL AXIS DETECTION APPARATUS

[75] Inventors: Kazuki Konishi, Tokyo; Yasuo Suda, Yokohama; Akihiko Nagano, Kawasaki, all of Japan

[73] Assignee: Canon Kabushiki Kaisha, Tokyo, Japan

[21] Appl. No.: 364,503

[22] Filed: Dec. 27, 1994

Related U.S. Application Data

[63] Continuation of Ser. No. 135,576, Oct. 13, 1993, abandoned, which is a continuation of Ser. No. 815,045, Dec. 31, 1991, abandoned.

[30] Foreign Application Priority Data

Jan. 8, 1991 [JP] Japan .................................. 3-011491
Jan. 8, 1991 [JP] Japan .................................. 3-011493

[51] Int. Cl.⁶ ...................................................... A61B 3/10
[52] U.S. Cl. .......................... 351/206; 351/205; 351/211
[58] Field of Search .................................... 351/200, 205, 351/211, 246, 209, 210

[56] References Cited

FOREIGN PATENT DOCUMENTS 2-209125  8/1990  Japan .
2-264632 10/1990  Japan .

Primary Examiner—William L. Sikes
Assistant Examiner—Hung Xuan Dang
Attorney, Agent, or Firm—Fitzpatrick, Cella, Harper & Scinto

[57] ABSTRACT

An apparatus for detecting the visual axis of an observer in accordance with light reflected by a photo-sensor by illuminating an eye of the observer includes a controller means for controlling the accumulation time of the photo-sensor or a quantity of light emitted by a light projector so that the reflected light is sufficient to permit the detection of the visual axis.

21 Claims, 9 Drawing Sheets

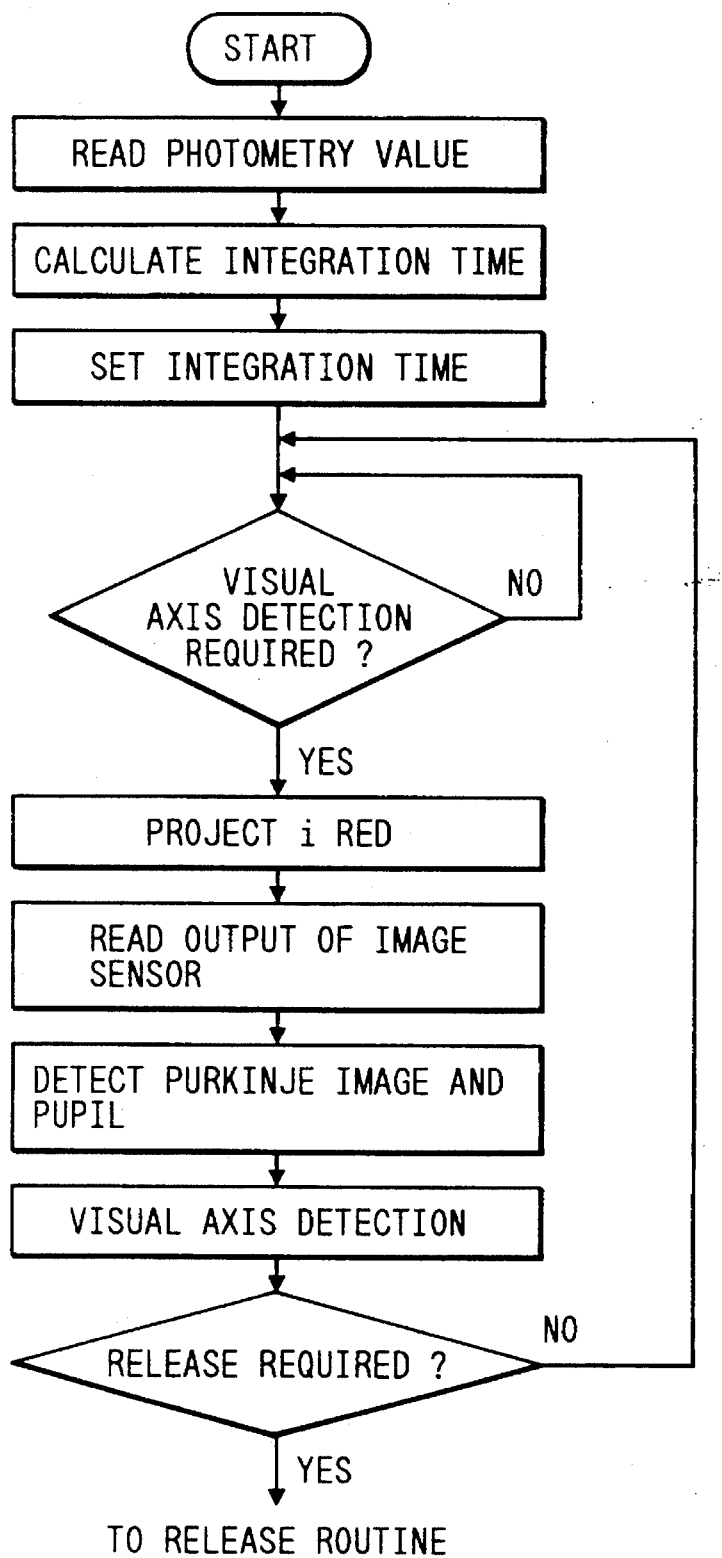

VISUAL AXIS DETECTION APPARATUS

This application is a continuation of application Ser. No. 08/135,576 filed Oct. 13, 1993, now abandoned, which is a continuation of application Ser. No. 07/815,045 filed Dec. 31, 1991, now abandoned.

BACKGROUND OF THE INVENTION

1. Field of the Invention

The present invention relates to a visual axis detection apparatus, and more particularly to a visual axis detection apparatus which irradiates an eyeball of an observer (photographer) with a light beam from light projection means, forms a first Purkinje image (cornea reflected image) due to reflected light from the eyeball and a pupil on an image sensor plane and detects the visual axis of the eyeball in accordance with positional coordinates of the images on the image sensor while properly controlling the accumulation time in detecting the light beam with the image sensor in order to permit high precision detection of the visual axis, and which is suitable for use in a still camera or a video camera.

2. Related Background Art

FIG. 9 shows a block diagram of a prior art visual axis detection apparatus.

Numeral 91 denotes a microprocessing unit (MPU) which carriers out various operations such as a visual axis calculation in accordance with positional information of a first Purkinje image and a pupil. Numeral 92 denotes a memory, numeral 93 denotes an interface circuit which has an A/D conversion function, numeral 97 denotes light projection means which projects an infrared ray, which is invisible to an observer, emitted from an infrared ray light emitting diode 97a to an eyeball (not shown) of the observer through a projection lens 97b, numeral 95 denotes a light emission control circuit which controls the light emission of the infrared light emitting diode 97a, and numeral 96 denotes a position sensor which detects the vertical/horizontal position of a camera when the visual axis detection apparatus is applied to the camera.

Numeral 94 denotes detection means which includes an image sensor 94a, a driver 94b and a lens 94c and focuses the first Purkinje image due to the reflected light from the eyeball and the pupil image onto the image sensor 94a through the lens 94c.

A method for detecting the visual axis of the eyeball in FIG. 9 has been proposed by Japanese Laid-Open Patent Application No. 2-209125 or 2-264632, in which the visual axis is detected by using two positional information of the first Purkinje image (cornea reflected image) due to the reflected light from the eyeball of the infrared ray emitted from the light projection means 97, and the pupil center calculated from the contours of the pupil.

The infrared ray from the projection means irradiates the eyeball of the observer from the front, and the position of a virtual image of the infrared light emitting diode generated by the reflection by the front plane of the cornea, that is, a so-called first Purkinje image, is detected by the image sensor. The position at which the first Purkinje image is generated corresponds to the position of the pupil center when a rotation angle of the eyeball is zero (the optical axis of the eyeball) and it deviates from the pupil center as the eyeball rotates.

The deviation (distance) between the first Purkinje image and the pupil center is substantially proportional to the sine of the rotation angle of the eyeball. Accordingly, the distance is determined from the positional information of the first Purkinje image and the pupil center, and the rotation angle and the visual axis correction are calculated to determine the visual axis of the photographer.

The accumulation time of the image sensor when the image sensor senses the light beam is set to an appropriate time while taking into consideration various conditions such as the emission luminance of the infrared light emitting diode, the sensitivity of the image sensor, an S/N ratio and an external light which is normally ancitipated in photographing, and the image sensor accumulates the light beam for the predetermined accumulation time.

In the prior art visual axis detection apparatus, the accumulation time of the image sensor when the image sensor senses the light beam is set in accordance with the conditions described above and the light beam is sensed for the preset accumulation time.

As a result, various problems may arise depending on the illumination of an anterior portion of the eyeball. For example, if the illumination is low, the contrast (a difference between output signals) of the pupil and the iris is low and it is difficult to detect the contour of the pupil. On the other hand, when the illumination is very high, the image sensor saturates and the difference between the output signals for the first Purkinje image and the iris, which inherently has a difference, disappears and it is impossible or difficult to detect the first Purkinje image.

SUMMARY OF THE INVENTION

It is an object of the present invention to provide a visual axis detection apparatus which permits high precision detection of a visual axis by properly controlling the accumulation time of an image sensor when the image sensor senses a light beam so that a signal having a sufficient contrast to detect a first Purkinje image and a pupil is produced within a dynamic range of the image sensor.

The visual axis detection apparatus of the present invention is characterized by the irradiation of a light beam from light projection means on the eyeball, the detecting of the position coordinates of the Purkinje image due to the reflected light from the eyeball and the position coordinates of the pupil by the detection means having the image sensor, and the determining of the visual axis of the eyeball in accordance with the position coordinates detected by the detection means while the integration time (accumulation time) of the image sensor and/or the light quantity of the light projection means are controlled by data measured by a photo-sensor which senses the brightness in the vicinity of the anterior eye portion of the eyeball.

The present invention is further characterized by limiting an upper limit of the accumulation time of the image sensor by a period of occurrence of a saccadic movement, or by an average or the maximum velocity of a smooth pursuit movement of the eyeball, a sensor pitch of the image sensor and an imaging magnification of the detection means.

In the present invention, the accumulation time of the image sensor is controlled by the output of the photo-sensor and the upper limit (longest time) of the accumulation time is limited by the value determined by the characteristic of the movement of the eyeball stored in memory means in order to permit the detection of the visual axis without regard to the luminance of the external light and free of a detection error due to the characteristic of movement of the eyeball.

BRIEF DESCRIPTION OF THE DRAWINGS

FIG. 7 shows a flow chart of Embodiment 2 of the present invention.

DETAILED DESCRIPTION OF THE PREFERRED EMBODIMENTS

Figure 1:
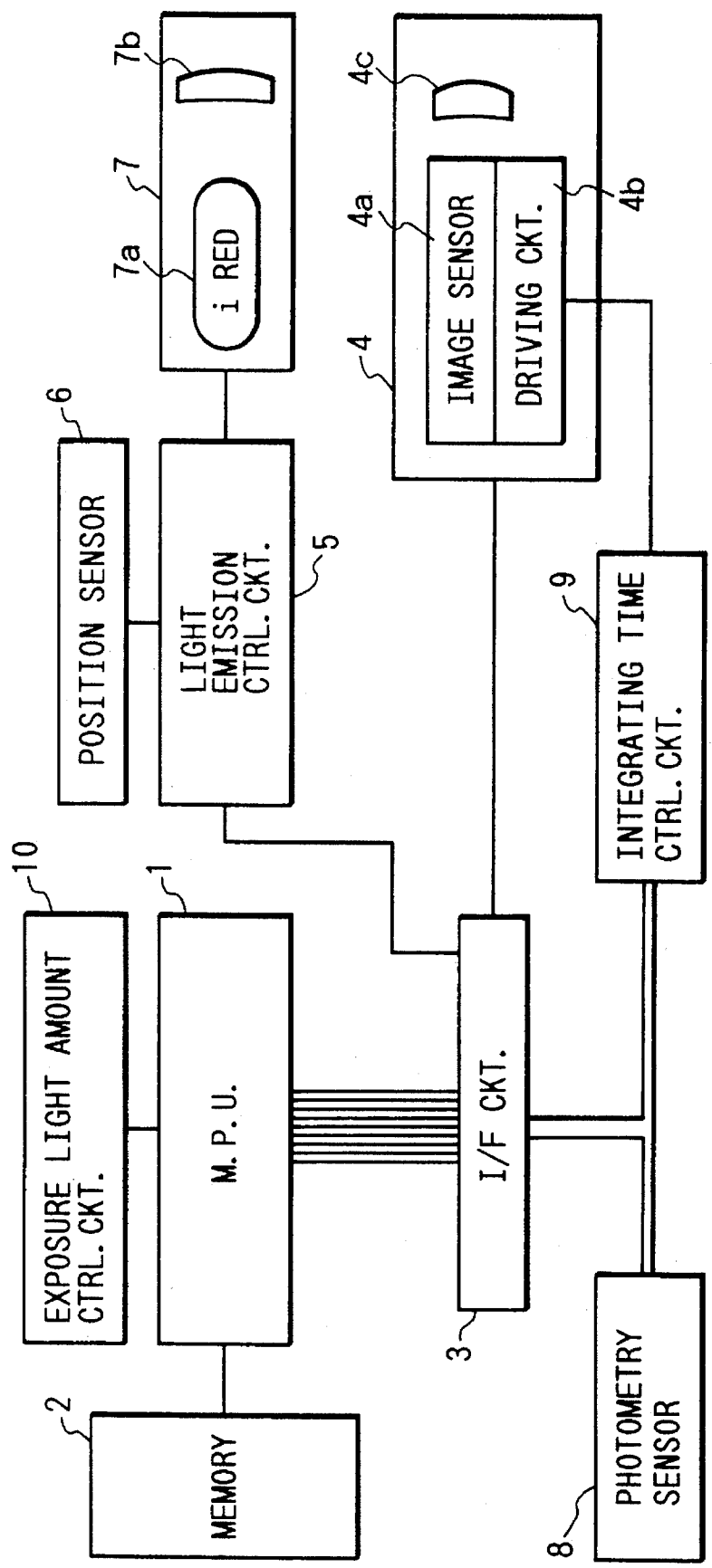
FIG. 1 shows a block diagram of Embodiment 1 of the present invention.
Figure 2A:
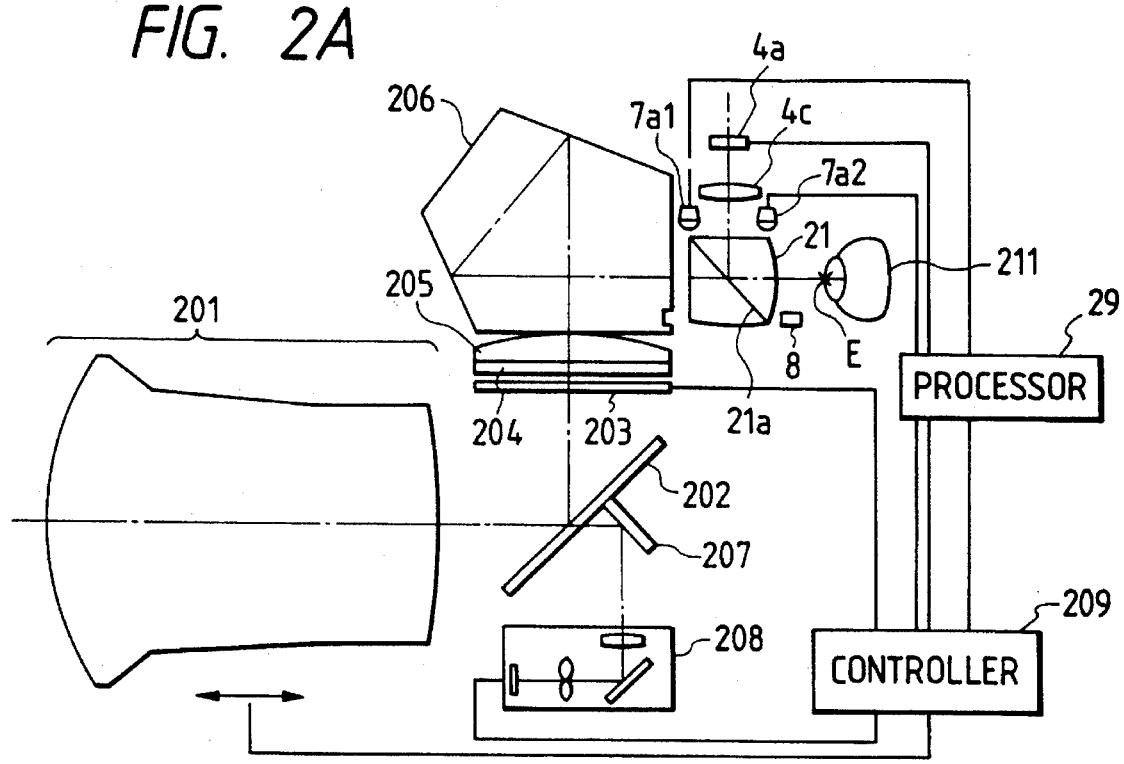
FIG. 2A shows a schematic view when the present invention is applied to a one-eye reflex type camera.
Figure 2B:
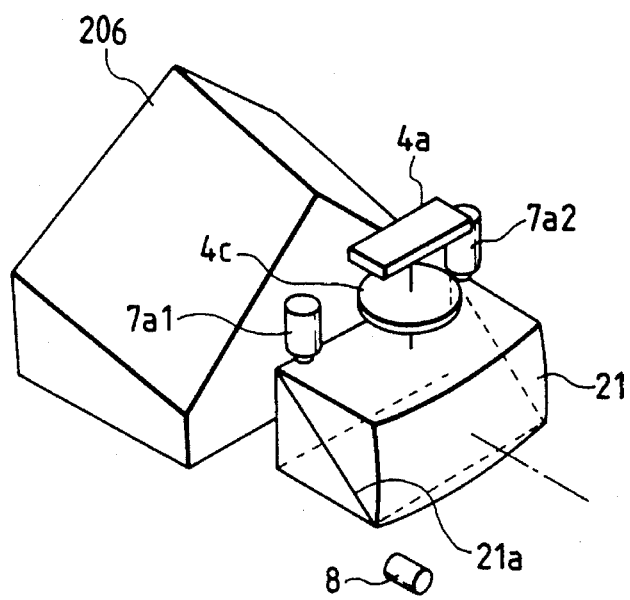
FIG. 2B shows a perspective view of a portion of FIG. 2A.

FIG. 1 shows a block diagram of Embodiment 1 of the present invention, FIG. 2A shows a schematic view when visual axis detection means of the present invention is applied to a single-lens reflex camera, and FIG. 2B shows a perspective view of a portion of FIG. 2A.

In FIG. 1, numeral 1 denotes a microprocessing unit (MPU) which carries out various operations such as calculation of a visual axis by using position information of a first Purkinje image and a pupil and calculation of exposure to an exposure control unit 10. Numeral 2 denotes a memory which, for example, stores a signal relating to the integration time of an image sensor. Numeral 3 denotes an interface circuit which has an A/D conversion function. Numeral 7 denotes light projection means which projects an infrared ray, which is invisible to an observer, emitted from an infrared light emitting diode 7a to the eyeball of the observer through a projection lens 7b. Numeral 5 denotes a light emission control circuit (light emission control means) which controls the light intensity of the infrared light emitting diode 7a. Numeral 6 denotes a position sensor which detects the vertical/horizontal position of a camera when it is applied to the camera.

Numeral 4 denotes detection means which includes an image sensor 4a, a driver 4b and a lens 4c and focuses the first Purkinje image due to the reflected right from the eyeball and the pupil onto the plane of the image sensor 4a through the lens 4c.

Numeral 8 denotes a photo-sensor which detects the illuminance of an anterior eye portion of the eyeball. Numeral 9 denotes an integrations time control circuit (integration time control means) which controls the integration time (accumulation time) of the image sensor 4a when the image sensor 4a senses the light beams of the first Purkinje image and the pupil in accordance with the signal from the photo-sensor 8.

A construction when the present invention is applied to a single lens reflex camera is explained with reference to FIGS. 2A and 2B.

Numeral 21 denotes an eye lens in which a dichroic mirror 21a which transmits a visible ray and reflects an infrared ray is obliquely mounted; it also functions as a light path splitter. Numeral 4a denotes an image sensor, numeral 4c denotes a lens and numerals 7a1 and 7a2 denote light sources such as light emitting diodes which are components of light projection means 7.

The image sensor 4a comprises a two-dimension array of photo-electric elements which is arranged at a position which is conjugate with the vicinity of the pupil of the eye located at a predetermined position (a usual eye point of a photographer who does not put eyeglasses) with respect to the lens 4c and the eye lens 21. Numeral 8 denotes a photo-sensor which is arranged in the vicinity of the eye lens 21.

Numeral 29 denotes a processing unit which performs the functions of visual axis correction calculation, visual axis correction data storage and visual axis calculation, and includes the MPU 1, the integration time control circuit 9, the light emission control circuit 5, the memory 2 and the interface circuit 3 of FIG. 1.

Numeral 201 denotes a photographing lens, numeral 202 denotes a quick return (QR) mirror, numeral 203 denotes a display device, numeral 204 denotes a focus plate, numeral 205 denotes a condenser lens, numeral 206 denotes a pentagonal prism, numeral 207 denotes a sub-mirror, numeral 208 denotes a multi-point focus detector which selects a plurality of areas in a photographing screen to detect the focal point in a known manner, and numeral 209 denotes a camera control unit which performs the functions of driving a display device in a finder, detecting and calculating the focal point and driving the lens.

In the present embodiment, a portion of the object light which is transmitted through the photographing lens 201 is reflected by the QR mirror 202 and the object image is focused in the vicinity of the focus plate 204. The object light diffused by a diffusion plane of the focal plate 204 is directed to an eyepoint E through the condenser lens 205, the pentagonal prism 206 and the eye lens 21.

The display device 203 may be a dual layer type guest-host liquid crystal display without a polarization plate and it displays a distance metering range (focal point detection position) in a view field of the finder.

A portion of the object light transmitted through the photographing lens 201 passes through the QR mirror 202, is reflected by the sub-mirror 207 and is directed to the multi-point focus detector 208 mounted on the bottom of the camera body. A photographing lens driver (not shown) drives in and out the photographing lens to adjust the focal point in accordance with the focus detection information of the points on the object selected by the multi-point focus detector 208.

A principle of the method for detecting the visual axis is same as that proposed in Japanese Laid-Open Patent Application No. 2-209125 or 2-264632.

In the present embodiment, the infrared rays emitted from the infrared light emitting diodes 7a1 and 7a2 are directed to the eye lens 21 from the top of the drawing, reflected by the dichroic mirror 21a and irradiate the eyeball 211 of the observer located in the vicinity of the eyepoint E. The infrared ray reflected by the eyeball 211 is reflected by the dichroic mirror 21a, and converged by the lens 4c to form an image on the image sensor 4a.

In the present embodiment, the visual axis of the eyeball is determined by the positions of the first Purkinje image and the pupil center formed on the image sensor 4a. The MPU 1 reads the image of the anterior eye portion of the eyeball including the first Purkinje image focused on the image sensor 4a, through the interface circuit 3 to determine the coordinates of the first Purkinje image and the coordinates of the pupil center calculated by the coordinates of a plurality of contours of pupil. It determines a relative amount of shift between the rotation angle of the eyeball of the observer and the camera, and the position of the visual axis on the finder system based on those coordinates. Those values are stored in the memory 2.

In the present embodiment, the integration time of the image sensor 4a is properly set to produce a signal from the image sensor 4a which is suitable for the calculation.

Specifically, in the present embodiment, the brightness in the vicinity of the anterior eye portion of the eyeball is measured by the photo-sensor and the integration time of the image sensor is controlled by the signal from the photo-sensor.

In the present embodiment, the integration time is varied by the integration time control circuit in accordance with the signal output from the photo-sensor and the upper limit of the integration time is limited in accordance with the movement characteristic of the eyeball stored in the memory 2 in a manner to be described later so that the signal output which is suitable for the calculation is always produced. In this manner, the visual axis of the eyeball is detected with high precision.

Figure 3:
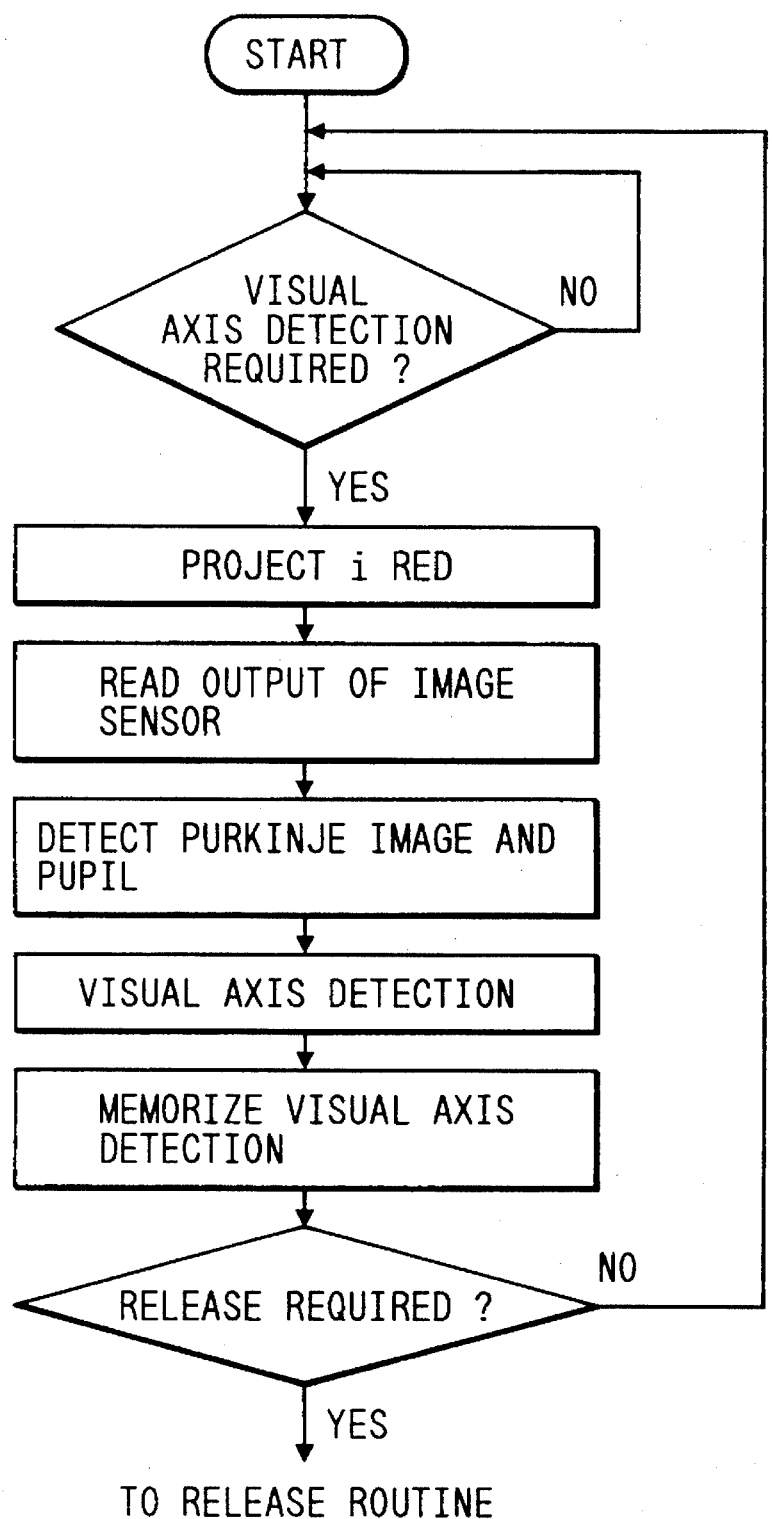
FIG. 3 shows a flow chart of Embodiment 1 of the present invention.

FIG. 3 shows a flow chart of an operation of the present embodiment. When a request to detect the visual axis is issued by depressing a visual axis mode switch (not shown), the MPU 1 starts the visual axis detection routine. When the visual axis detection routine is started, the MPU 1 causes the infrared light emitting diode to emit the infrared ray in accordance with the light quantity and the integration time of the image sensor determined in the manner to be described later, and starts the integration.

After the integration, the MPU 1 reads the output of the image sensor to determine the positions of the first Purkinje image, the pupil and the visual axis of the observer, and stores them in the memory as required. When a request to release is issued, a release routine is started.

In the present embodiment, the upper limit of the integration time is determined by the following two methods in accordance with the movement characteristic of the eyeball, and it is stored in the memory 2.

In a first method, the upper limit is determined by a period of occurrence of a saccadic movement. The saccadic movement has a movement time of 1/20–1/100 second, a maximum speed of 300 degrees/sec and a period of occurrence of no less than 0.2 second. During this movement the visual function is extremely diminished in the movement period from 0.05 second prior to the start of the movement to the end of movement (saccadic suppress).

In general, when the integration time is too long, the saccadic movement takes place in the integration time immediately after the preceding saccadic movement and the position of the visual axis after the former saccadic movement cannot be detected. Thus, the locus of the visual axis is not followed.

Further, since the position of the visual axis during the saccadic movement makes no sense in view of the saccadic suppress phenomenon, it is not necessary to shorten the integration time in order to determine such a position.

Accordingly, the integration time in the present embodiment is limited to be no longer than 0.1 second.

Figure 4:
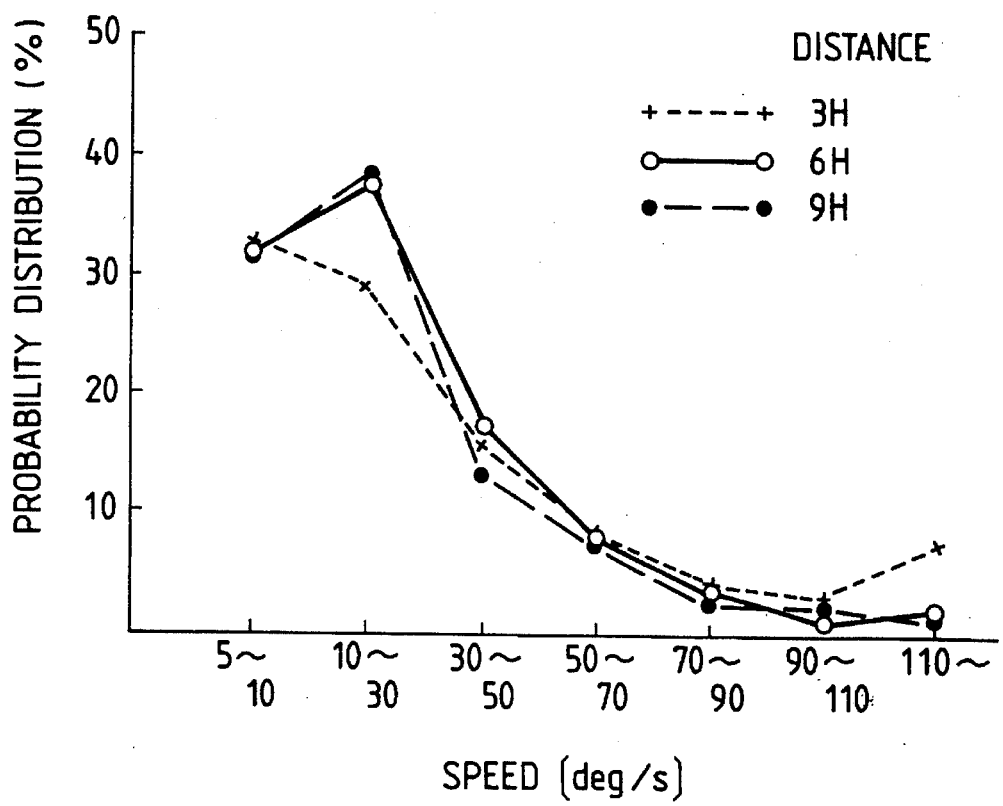
FIG. 4 illustrates the velocity of an eyeball movement.

In a second method, the upper limit is determined by the velocity of a follow movement. The follow movement is a slow and smooth movement of the eyeball which takes place when the eyeball slowly follows a moving object which moves at a velocity of 30–35 degrees/second. It is caused when the eyeball continuously and stably follow the object. It also includes a saccadic movement. An example of probability distribution of the velocity in a TV image is shown in FIG. 4.

In the present embodiment, the maximum speed of the follow movement in an average status is assumed to be 30 degrees/second.

In this method, the integration time of the image sensor is set such that the change in the image of the anterior eye portion of the eyeball caused by the follow movement is within the pitch of pixels on the image sensor. The change in the image on the image sensor is within the pitch of pixels when the following approximation formula is met.

$$P \geq \beta \cdot R \cdot \omega T \qquad (1)$$

where R is a distance from a rotation center of the eyeball to a front plane of the cornea, $\omega$ (rad/sec) is the rotation speed of the eyeball, $\beta$ is the focusing magnification of the lens system of the detection means, P is the pitch of the pixels of the image sensor and T is the integration time. From the above formula, following equation can be obtained.

$$T \leq \frac{P}{\beta \cdot R \cdot \omega} \qquad (2)$$

For example, when the pitch of the pixels of the image sensor is 30 μm, the focusing magnification of the detection means is 0.2, the distance R is 13.5 mm and the rotation speed $\omega$ is $\pi/6$ rad/sec, $$T \leq 0.0213 (\text{sec})$$

Thus, the integration time is set to be no longer than 20 msecond.

In the present embodiment, whether the first method or the second method is to be selected is determined by what information of the visual axis is used and what is to be controlled.

In the present embodiment, the first method is selected when the control is to be done by using locus information of the visual axis. For example, it is used in the control in which the range of distribution of the visual axis is known and the focal distance of the lens system of the detection means which covers the range is automatically controlled (auto-zooming control) or the control in which a distance metering view field is moved with the movement of the object (auto-tracking AF).

On the other hand, the second method is selected when an auto-focus (AF) point or an autoexposure (AE) point is to be determined for a still object by using relatively precise visual axis position information, or the instructions of the photographer are to be inputted by the visual axis.

The second method may be selected depending on the pitch of the pixels of the image sensor or the focusing magnification of the lens system. In the present embodiment, the upper limit of the integration time may be, in some cases, longer than that determined by the first method.

Figure 6:
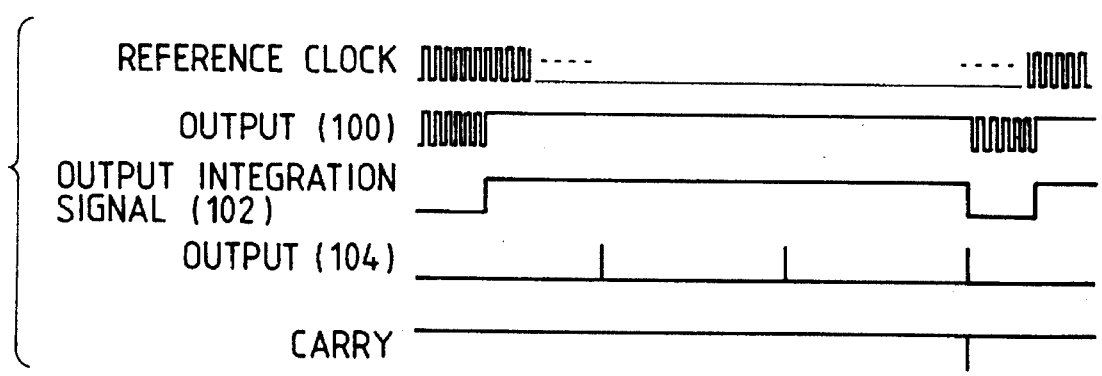
FIG. 6 shows a timing chart of the accumulation time control circuit of FIG. 5.
Figure 5:
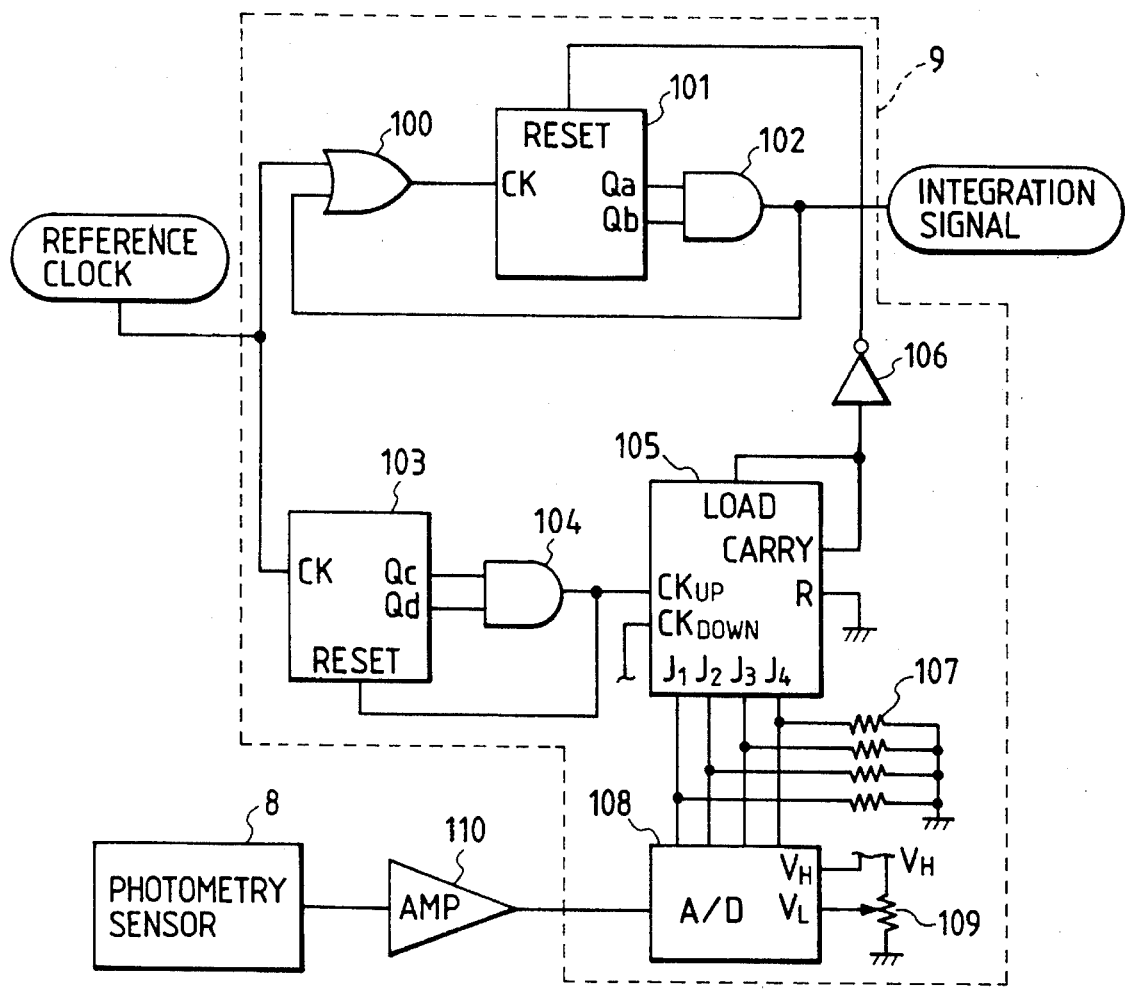
FIG. 5 shows an accumulation time control circuit of Embodiment 1 of the present invention.

FIG. 5 shows a circuit diagram of the integration time control circuit 9 of FIG. 1, and FIG. 6 shows a timing chart of the integration time control circuit 9 of FIG. 5.

Numeral 100 denotes an OR gate, numerals 101 and 103 denote counters, numerals 102 and 104 denote AND gates, numeral 105 denotes a count-of-N counter having a preset function, numeral 106 denotes an inverter, numeral 107 denotes a resistor for stabilizing an input to the counter 105, numeral 108 denotes an A/D converter, and numeral 109 denotes a dividing resistor to apply a minimum voltage for the A/D conversion.

When a main switch of the camera is turned on and a reference clock is supplied, one input to the OR gate 100 is Low and the reference clock is applied from the output of the OR gate 100 to the counter 101. When $(2^a+2^b)$ reference clocks are applied, the output of the AND gate 102, that is, the integration signal changes to High. The one input to the OR gate 100 also changes to High and the output of the OR gate 100 is fixed to High. Thus, the supply of the reference clock is stopped and the integration signal is kept High until a reset voltage is applied to a reset terminal of the counter 101.

The reference clock is also supplied to the counter 103, when $(2^c+2^d)$ reference clocks are applied, the output of the AND gate 104 changes to High, the reset voltage is applied to the reset terminal of the counter 103, and the output of the AND circuit 104 changes to Low.

Since the reference clock is always applied to the counter 103, a short duration pulse is produced at the output terminal of the AND gate 104 each time the $(2^c+2^d)$ pulses are applied to the counter 103. The short duration pulse is applied to the count-of-N counter 105 having the preset function.

When (N−M+1) short duration pulses are applied to the count-of-N counter 105, the output at the CARRY terminal changes from High to Low, where M is a preset value at preset terminals ($J_1$–$J_4$ in FIG. 5). When the output at the CARRY terminal is inverted, the reset voltage is applied to the reset terminal of the counter 101 through the inverter 106 so that the output of the AND gate 102, that is, the integration signal changes to Low. The one input to the OR gate also changes to Low and the reference clock is again supplied to the counter 101. Then, the above operation is repeated.

As described above, the integration signal is High when $(2^a+2^b)$ reference clocks are applied, and Low when $(2^c+2^d) \times (N-M+1)$ reference clocks are applied. Thus, the integration time is given by:

$$T=\{(2^c+2^d)(N-M+1)-(2^a+2^b)\}/f_{CK} \qquad (3)$$

where $f_{CK}$ is a frequency of the reference clock.

In the present embodiment, the integration time is varied by a combination of a, b, c, d, N, M and $f_{CK}$.

The change of the integration time in accordance with the output of the photo-sensor 8 (the brightness in the vicinity of the anterior eye portion of the eyeball) is now explained.

The output of the photo-sensor 8 is applied to the A/D converter 108 through the amplifier 110. The A/D converted output terminals are connected to the preset terminals of the count-of-N counter 105. Thus, the larger the output of the photo-sensor is, that is, the higher the brightness in the vicinity of the anterior eye portion of the eyeball, the larger is the digital output of the A/D converter 108, and the larger is the preset value M of the count-of-N counter 105 and the shorter is the integration time given by the formula (3).

On the other hand, the zero level $V_L$ and the maximum level $V_H$ of the A/D conversion are determined by the dividing resistor 109 and the constant voltage $V_H$, respectively. When the input voltage to the A/D converter 108 is lower than the voltage $V_L$ determined by the dividing resistor 109, all preset terminals of the count-of-N counter 105 are set to Low (M=0).

As seen from the formula (3), the maximum integration time is given. Thus, a, b, c, d, N and $f_{CK}$ in the formula (3) are determined to define the maximum integration time, and the zero level voltage $V_L$ is applied to determine the corresponding output of the photo-sensor. In this manner, the maximum integration time is set when the brightness in the vicinity of the anterior eye portion of the eyeball is lower than a certain level, and the integration time is shortened as the brightness increases.

In FIG. 5, although the AND gate has two inputs and the count-of-N counter having the preset function is the hexadecimal (4 bits) counter, they are not limited in any practical circuit. For example, when the AND gate 102 has $l_1$ inputs and $l_2$ inputs, the integration time T is given by:

$$T=\left\{\sum_{l_i=1}^{l_2} 2^i (N-M+1) - \sum_{l_i=1}^{l_1} 2^i\right\} / f_{CK}$$

It is preferable to use a photo-sensor for controlling the exposure of the camera as the photo-sensor 8. In this case, the output may include some error due to the distance between the photographer and the object but such an error is usually within a permissible range.

Figure 8:
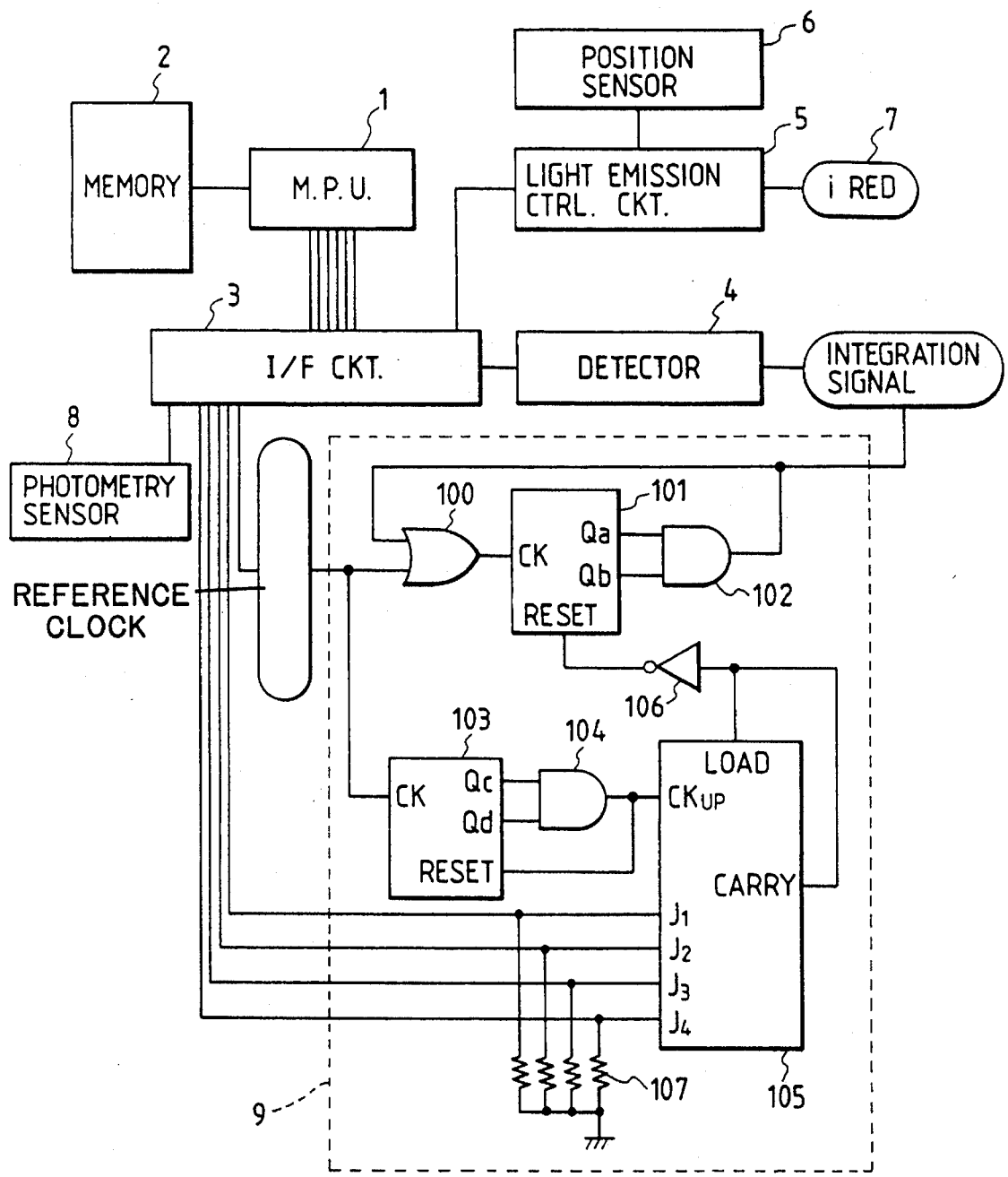
FIG. 8 shows a block diagram of Embodiment 2 of the present invention.
Figure 9:
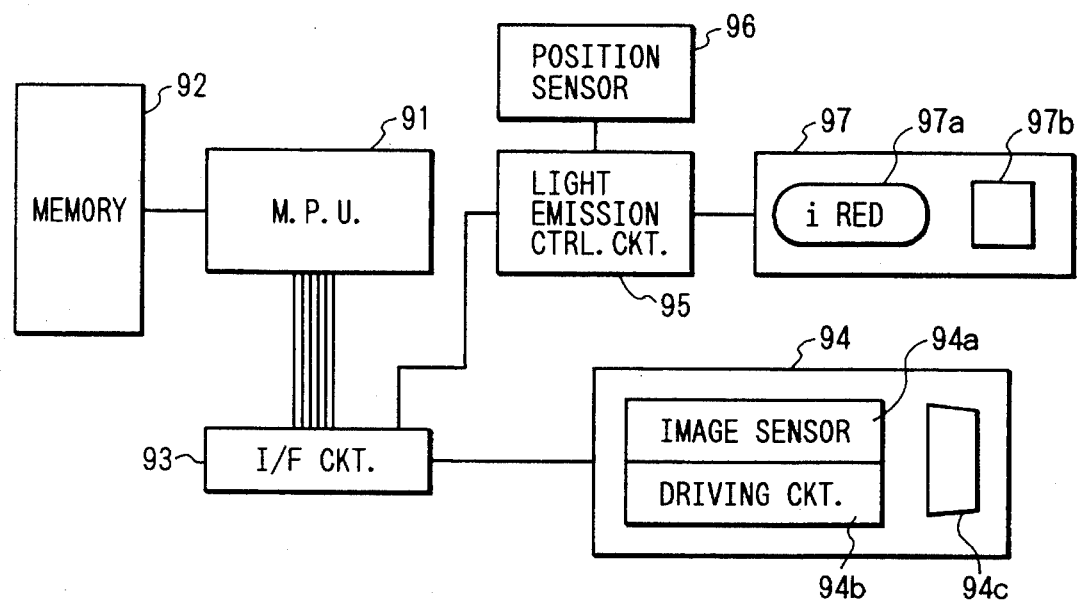
FIG. 9 shows a schematic view of a prior art visual axis detection apparatus.

FIG. 7 shows a flow chart of Embodiment 2 of the present invention, and FIG. 8 shows a block diagram of Embodiment 2 of the present invention.

The present embodiment is characterized by the MPU 1 calculating and setting the integration time in accordance with the output of the photo-sensor 8.

The MPU 1 first reads the output of the photo-sensor 8 through the interface circuit 3. It calculates the integration time based on the output of the photo-sensor 8. The upper limit is set in the calculation. This is done by setting the preset value M of the count-of-N counter 105 having the preset function to $(V-V_L)/(V_H-V_L)*N$. If M is negative, M is set to zero, and the maximum value of M is set to N. V is the output voltage of the photo-sensor 8, and $V_H$ and $V_L$ are constants determined to set the integration time. The integration time T in the circuit shown in FIG. 8 is given by:

$$T=\{(2^c 2^d)(N-M+1)-(2^a+2^b)\}/f_{CK} \qquad (3)$$

M is determined in the manner described above.

The MPU 1 then sets the value M to the preset terminals ($J_1$–$J_4$) of the count-of-N counter 105 through the interface circuit 3. When a request to detect the visual axis is issued by the camera, the MPU 1 starts the visual axis detection routine. It reads the output of the image sensor, determines the positions of the first Purkinje image and the pupil contour and calculates the visual axis.

In the present embodiment, the AND gate may have other than two inputs as it does in Embodiment 1. Any type of count-of-N counter 105 may be used. The photo-sensor 8 is shared by the sensor for controlling the exposure of the camera.

In the above embodiments, the control unit which controls the accumulation time of the image sensor is used. Another embodiment which controls the light intensity of the light projection means to precisely detect the visual axis is now explained.

In the following embodiment, the integration time of the image sensor is varied in accordance with the output of the photo-sensor, and the light quantity of the infrared light emitting diode for forming the first Purkinje image is controlled thereby so that the image sensor always produces a signal output which is suitable for the calculation to precisely detect the visual line of the eyeball.

For example, when the luminance of the external light is high, the integration time of the image sensor is set short and the light quantity of the infrared light emitting diode is increased accordingly. Where the anterior eye portion of the eyeball is fully illuminated by the external light, the contrast of the boundary between the pupil and the iris is relatively high and a good image for the detection of the pupil is produced.

However, since the signal intensity of the iris is high, the contrast of the signal is low when the first Purkinje image is formed on the iris and it is difficult to detect the first Purkinje image. When the luminance of the external light is high, the pupil diameter is small and it is likely that the first Purkinje image is formed on the iris.

In the present embodiment, the integration time of the image sensor is shortened in such a situation to lower the intensity of the overall signal and the light emitting quantity of the infrared light emitting diode is increased to increase the signal intensity of the first Purkinje image.

On the other hand, when the luminance of the external light is low, the integration time of the image sensor is extended and the light emission quantity of the infrared light emitting diode is reduced accordingly. Where the anterior eye portion of the eyeball is not fully illuminated by the external light, the contrast of the boundary between the pupil and the iris is low and it is difficult to detect the pupil.

On the other hand, since the intensity of the first Purkinje image is substantially constant without regard to the external light, it is easy to detect it. In the present embodiment, the integration time of the image sensor is extended in such a case to increase the intensity of the overall signal to increase the contrast of the boundary between the pupil and the iris, and the light emission quantity of the infrared light emitting diode is reduced to lower the intensity of the first Purkinje image to prevent the saturation of the image sensor.

When the integration time of the image sensor is long, the light emission quantity of the infrared light emitting diode is reduced to reduce the energy of the infrared light emitting diode irradiated to the eyeball to protect the eyeball.

A method for setting the light emission intensity of the infrared light emitting diode 8 by the light emission control circuit 5 is now explained.

Figure 10:
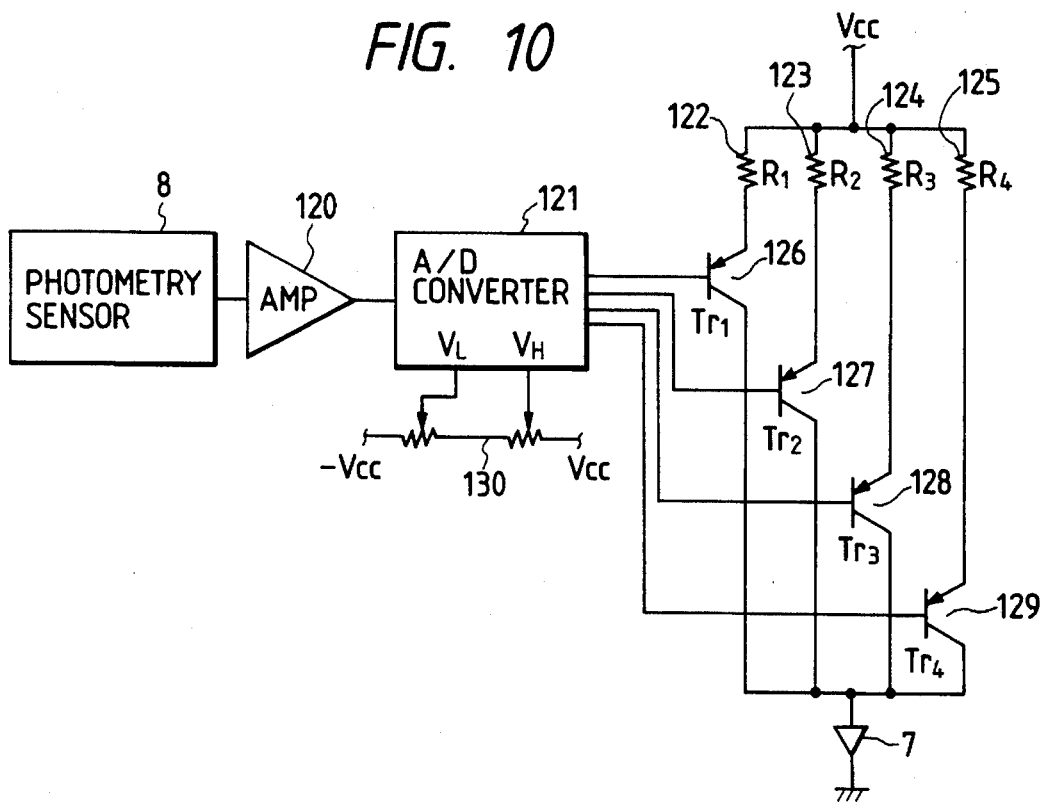
FIG. 10 shows a schematic view of a light emission control circuit in another embodiment of the present invention.

FIG. 10 shows a circuit diagram of the light emission control circuit 5. Numeral 120 denotes an amplifier, numeral 121 denotes an A/D converter, numerals 122, 123, 124 and 125 denote resistors which define currents flowing through the infrared light emitting diode, numerals 126, 127, 128 and 129 denote transistors which function as switching devices, and numeral 130 denotes a resistor which defines a minimum voltage level of the A/D conversion.

The output of the photo-sensor 8 is amplified to a level appropriate for the A/D conversion by the amplifier 120 and it is supplied to the A/D converter 121. The A/D converted digital signal is sent to the transistors 126, 127, 128 and 129 so that the transistors are turned on and off in accordance with the bit values of the digital signal. The transistors corresponding to the bit "1" are turned on and the other transistors are turned off.

On the other hand, the resistances $R_1$, $R_2$, $R_3$ and $R_4$ of the resistors 122, 123, 124 and 125 are set to $R_1:R_2:R_3:R_4 = 8:4:2:1$, for example. As a result, the current flowing in the infrared light emitting diode 7a is proportional to the digital output of the A/D converter 121 (which corresponds to the output of the photo-sensor 8).

Since the light emission quantity of the infrared light emitting diode 7a is generally proportional to the current flowing therethrough, the light emission quantity of the infrared light emitting diode 7a is substantially proportional to the output of the photo-sensor 8.

In the circuit of FIG. 10, the minimum digital output of the A/D converter 121 is "1". In the present embodiment, the minimum level of the A/D conversion is determined by the resistor 130. The amplifier 120 may be either a linear amplifier or a non-linear amplifier. The A/D converter 121 is of 4-bit type in the present embodiment, although it is not restrictive. The photo-sensor 8 may be a photo-sensor for controlling the exposure of the camera. In this case, a certain error is included in the output due to a distance between the photographer and the object, but it is usually within a permissible range.

Figure 11:
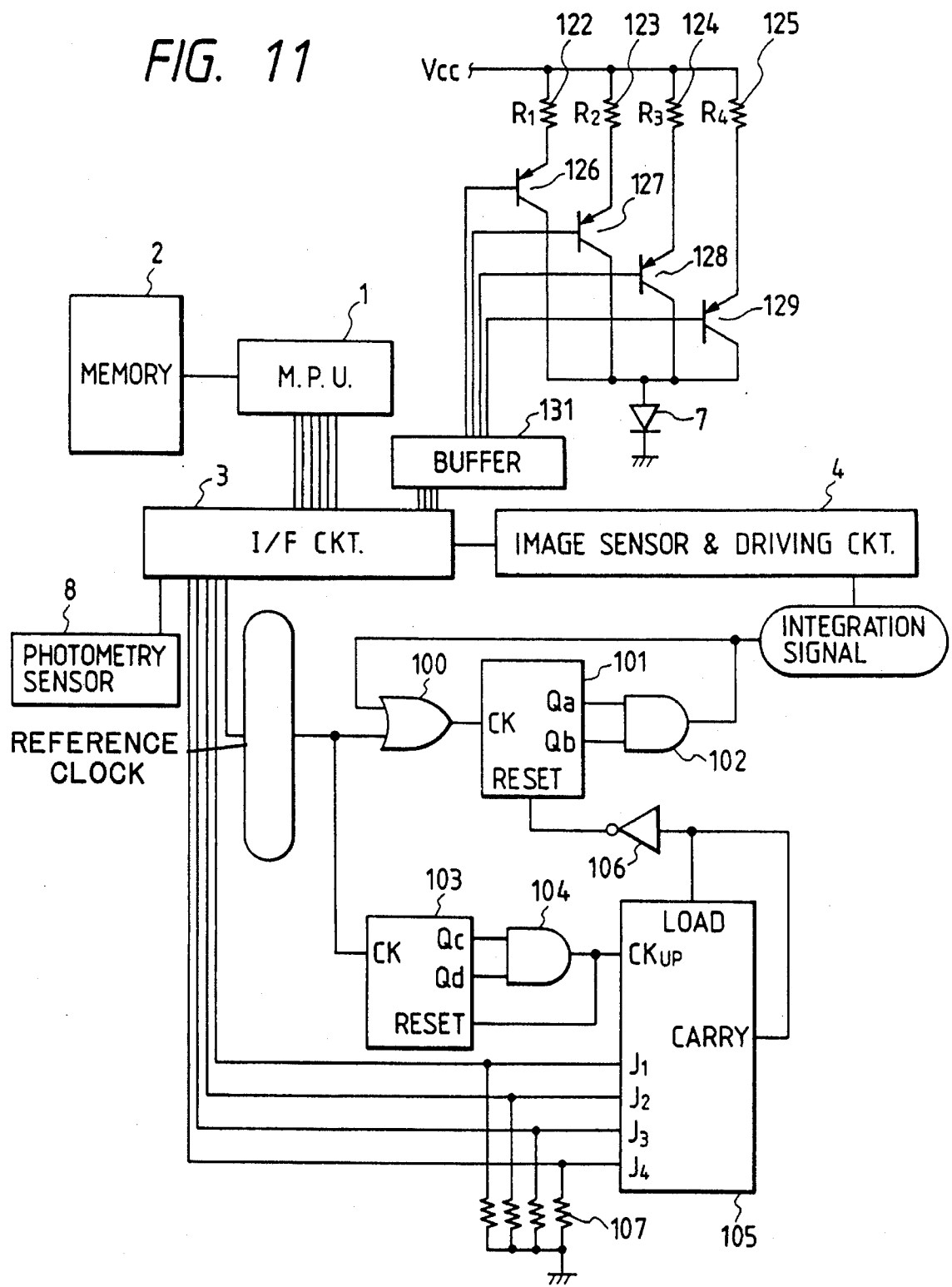
FIG. 11 shows a block diagram of other embodiment of the present invention.

FIG. 11 shows a block diagram of other embodiment of the present invention.

The present embodiment is characterized by that the MPU 1 calculates and sets the integration time T of the image sensor 4a and the light emission quantity I of the infrared light emitting diode 7a (in actual, a constant D which is proportional to the light emission quantity I is calculated by the MPU 1) in accordance with the output of the photo-sensor 8.

In the present embodiment, the MPU 1 reads the output of the photo-sensor 8 through the interface circuit 3. It sets the integration time of the image sensor 4a in accordance with the output of the photo-sensor 8. This is done by setting the value M corresponding to the integration time T to the count-of-N counter 105 having the preset function shown in FIG. 11. The value M is represented by $M=(V-V_L)/(V_H-V_L)*N$, and when M is negative, M is set to zero and the maximum value of M is set to N, where V is the output voltage of the photo-sensor 8, and $V_H$ and $V_L$ are constants determined to set the integration time, which correspond to the anticipated maximum and minimum values of the output of the photo-sensor 8. When the value M is set in the count-of-N counter 105, the integration time T is given by:

$$T = \frac{(2^c + 2^d)(N - M + 1) - (2^a + 2^b)}{F_{CK}} \quad (3)$$

The value M is determined to attain a desired integration time T. After the value M has been calculated, the MPU 1 sets the value M to the preset terminals ($J_1$–$J_4$) of the count-of-N counter 105.

Then, the MPU 1 determines the light emission quantity I of the infrared light emitting diode 7a and the constant D to set the light emission quantity I. The light emission intensity I is determined by:

$$I = E/T$$

where E is an energy irradiated to the eyeball (which is determined in accordance with a safety standard of a laser and it is usually set to 1/10 of a permissible range of the laser irradiation) and T is the integration time calculated in the manner described above.

The light emission quantity I is constant without regard to the integration time in order to assume the safety of the visual axis detection apparatus. The process to calculate the constant D is now explained.

The light emission quantity I is given by $$I = \eta \cdot V_{cc}/R$$

where $\eta$ is a light emission efficiency of the infrared light emitting diode 7a, Vcc is the power supply voltage of the circuit and R is the apparent resistance of the circuit. The transistor is turned on and off in accordance with the constant D so that the resistance R is determined. In the circuit of FIG. 11, $$I = \frac{\eta V_{cc} D}{8R_1}$$

where $R_1$ is a minimum resistance among the resistors 122–125 and the resistances $R_t$, $R_2$, $R_3$ and $R_4$ meet a relation of $8R_1=4R_2=2R_3=R_4$.

In the present embodiment, the constant. D is determined so that the desired light emission quantity I is attained and it is set through the interface circuit 3 and the buffer 131.

In the present embodiment, the integration time T and the light emission quantity I are set, and when the request to detect the visual axis is then issued by the camera, the visual axis detection routine is started in the visual axis detection routine, the MPU 1 causes the infrared light emitting diode to emit the infrared ray in accordance with the light emission quantity as mentioned above and integration time, and starts the integration. After the integration, it reads the output of the image sensor to detect the first Purkinje image and the pupil and determines the visual axis position of the photographer based on those value, and stores them in the memory as required. When a request to release is issued, it starts the release routine.

In the present embodiment, the AND gate may have other than two inputs and any type of count-of-N counter 105 may be used as they are in Embodiment 1.

The number of transistors used to set the light emission intensity is not limited to four but any number of transistors may be used. The output signal of the image sensor 4a may be used as the output of the photo-sensor.

In accordance with the present invention, the integration time of the image sensor and the light emission quantity of the light projection means when the image sensor detects the light beam are properly controlled so that the signal having sufficient contrast to detect the first Purkinje image and the pupil is produced within the dynamic range of the image sensor. Thus, the visual axis detection apparatus which attains the high precision detection of the visual axis is provided.

The present invention is characterized by determining that the integration time of the image sensor in accordance with the output of the photo-sensor and varying the light emission quantity of the infrared light emitting diode for forming the first Purkinje image with the integration time, that is, the light emission quantity is increased when the luminance of the external light is high where the integration time is short, and the light emission quantity is decreased when the luminance of the external light is low where the integration time is long. In this manner, a good image of the anterior eye of the eyeball is produced without being affected by the condition of the external light and the high precision of the visual axis is attained while the energy irradiated to the eyeball (the product of the light emission quantity and the light emission time) is kept constant to assure the safety of the eyeball.

What is claimed is:

1. A visual axis detection apparatus comprising:

light emission means for illuminating an eye of an observer;

means having a plurality of sensor elements for storing light from the eye in a form of electrical energy and producing an electrical signal;

means for forming information relating to the visual axis of the observer in accordance with the electrical signal;

photometering means for photometering the vicinity of the eye of the observer and producing a photometering signal; and control means for controlling the accumulation time of the electrical energy in accordance with the photometering signal of said photometering means.

2. A visual axis detection apparatus according to claim 1 further comprising exposure control means for controlling the exposure of a film in accordance with the photometering signal of said photometering means.

3. A visual axis detection apparatus according to claim 1 further comprising light emission quantity control means for controlling the light emission quantity of said light emission means in accordance with the photometering signal.

4. A visual axis detection apparatus comprising:

light emission means for illuminating an eye of an observer;

means, having a plurality of sensor elements, for storing light from the eye in a form of electrical energy and for photometering the vicinity of the eye of the observer;

means for forming information relating to the visual axis of the observer in accordance with the storing of light by said storing and photometering means; and control means for controlling the light emission quantity of said light emission means in accordance with the photometering performed by said storing and photometering means.

5. A visual axis detection apparatus according to claim 4 further comprising exposure control means for controlling the exposure of a film in accordance with the photometering of said storing and photometering means.

6. A visual axis detection apparatus according to claim 4 further comprising control means for controlling the accumulation of time of the storing and photometering means in accordance with the photometering performed by said storing and photometering means.

7. A visual detection apparatus according to claim 4, wherein said storing and photometering means comprises a single means performing both functions.

8. A visual axis detection apparatus according to claim 4, wherein said storing and photometering means comprises separate means for storing and means for photometering, wherein said storing means produces an electrical signal, wherein said photometering produces a photometering signal, wherein said forming means forms information relating to the visual axis in accordance with the electrical signal, and wherein said control means controls the light emission quantity in accordance with the photometering signal.

9. A visual axis detection apparatus comprising:

illumination means for illuminating an eyeball of an observer;

photodetecting means, receiving light reflected by the eyeball, for detecting an image of the eyeball and for photometering the vicinity of the eyeball;

forming means for forming information relating to a visual axis of the observer in accordance with the image detecting by said photodetecting means; and control means for controlling said photodetecting means so that said photodetecting means outputs a proper electrical signal used by said forming means to form information relating to the visual axis in accordance with the photometering performed by said photodetecting means.

10. A visual axis detection apparatus according to claim 9, wherein said control means controls the accumulation time of said photodetecting means.

11. A visual axis detection apparatus according to claim 9, wherein said means for photodetecting and photometering means comprises a single means performing both functions.

12. A visual axis detection apparatus according to claim 9, wherein said photodetecting means comprises separate means for detecting an image of the eyeball and means for photometering the vicinity of the eyeball, wherein said detecting means produces an electrical signal, wherein said photometering means produces a photometering signal, wherein said control means controls said photodetecting means to output a proper electrical signal in accordance with the photometering signal produced by said photometering means.

13. A visual axis detection apparatus comprising:

illumination means for illuminating an eyeball of an observer;

photodetecting means, receiving light reflected by the eyeball, for detecting an image of the eyeball and for photometering the vicinity of the eyeball;

forming means for forming information relating to a visual axis of the observer in accordance with the image detecting by said photodetecting means; and control means for controlling the detecting of an image of the eyeball by said photodetecting means in accordance with the photometering performed by said photodetecting means.

14. A visual axis detection apparatus according to claim 13, wherein said control means controls the accumulation time of said photodetecting means.

15. A visual axis detection apparatus, according to claim 13, wherein said photodetecting means for photodetecting and photometering comprises a single means for performing these functions.

16. A visual axis detection apparatus, according to claim 13, wherein said photodetecting means comprises separate means for detecting an image of the eyeball and means for photometering the vicinity of the eyeball, wherein said detecting means produces an electrical signal and said photometering means produces a photometering signal, wherein said forming means forms information relating to the visual axis in accordance with the electrical signal, and wherein said control means controls said detecting means in accordance with the photometering signal.

17. A visual axis detection apparatus comprising:

light emission means for illuminating an eye of an observer;

means, having a plurality of sensor elements, for storing light from the eye in a form of electrical energy and for photometering the vicinity of the eye of the observer;

means for forming information relating to the visual axis of the observer in accordance with the storing by said storing and photometering means; and control means for controlling the accumulation time of the electrical energy in accordance with the photometering by said means for storing and photometering means.

18. A visual axis detection apparatus according to claim 17, wherein said means for storing and photometering comprises a single means performing both functions.

19. A visual axis detection apparatus according to claim 17, wherein said means for storing and photometering comprises separate means for storing and means for photometering.

20. A visual axis detection apparatus comprising:

light emission means for illuminating an eye of an observer;

means, having a plurality of sensor elements, for storing light from the eye in the form of electrical energy and producing an electrical signal;

means for generating information relating to the visual axis of the observer in accordance with the photometering means for photometering the vicinity of the eye of the observer and producing a photometering signal; and control means for controlling an emission amount of said light emission means based on the photometering signal.

21. A visual axis detection apparatus comprising:

illumination means for illuminating an eye of an observer;

photodetecting means, receiving light reflected by the eye, for detecting an image of the eye;

generating means for generating information relating to a visual axis of the observer in accordance with the image detecting by said photodetecting means; and control means for controlling an emission amount of said illumination means in accordance with an output of said photodetecting means.

* * * * *

UNITED STATES PATENT AND TRADEMARK OFFICE
CERTIFICATE OF CORRECTION

PATENT NO. : 5,508,759
DATED : April 16, 1996
INVENTOR(S) : KAZUKI KONISHI, ET AL.

It is certified that error appears in the above-indentified patent and that said Letters Patent is hereby corrected as shown below:

ON THE TITLE PAGE:

[57] ABSTRACT:

Line 3, "means" should be deleted.

COLUMN 1:

Line 28, "carriers" should read --carries--.

Line 35, "97ato" should read --97a to--.

Line 47, "axis-of" should read --axis of--.

COLUMN 3:

Line 25, "other" should read --another--.
Line 56, "right" should read --light--.

COLUMN 4:

Line 15, after "put" insert --on--.

UNITED STATES PATENT AND TRADEMARK OFFICE
CERTIFICATE OF CORRECTION

PATENT NO. : 5,508,759　　　　Page 2 of 3
DATED : April 16, 1996
INVENTOR(S) : KAZUKI KONISHI, ET AL.

It is certified that error appears in the above-indentified patent and that said Letters Patent is hereby corrected as shown below:

COLUMN 6:

Line 8, "follow" should read --follows--.

Line 28, "formula," should read --formula, the--.

COLUMN 7:

Line 14, "signal" should read --signal,--.

Line 37, "signal" should read --signal,--.

COLUMN 8:

Line 23, "a" should read --the--.

COLUMN 10:

Line 14, "other" should read --another--.

UNITED STATES PATENT AND TRADEMARK OFFICE
CERTIFICATE OF CORRECTION

PATENT NO. : 5,508,759 Page 3 of 3
DATED : April 16, 1996
INVENTOR(S) : KAZUKI KONISHI, ET AL.

It is certified that error appears in the above-indentified patent and that said Letters Patent is hereby corrected as shown below:

COLUMN 11:

Line 21, "value," should read --values,--.

Line 39, "that" should be deleted.

COLUMN 14

Line 24, after "the" (second occurrence) insert --electrical signal;--.

Signed and Sealed this

Twentieth Day of August, 1996

Attest:

BRUCE LEHMAN

*Attesting Officer*    *Commissioner of Patents and Trademarks*